United States Patent [19]

Dusza et al.

[11] 4,281,000

[45] Jul. 28, 1981

[54] SUBSTITUTED PYRAZOLO (1,5-A)PYRIMIDINES AND THEIR USE AS ANXIOLYTIC AGENTS

[75] Inventors: John P. Dusza; Jay D. Albright, both of Nanuet, N.Y.

[73] Assignee: American Cyanamid Company, Stamford, Conn.

[21] Appl. No.: 124,686

[22] Filed: Feb. 26, 1980

Related U.S. Application Data

[63] Continuation-in-part of Ser. No. 55,941, Jul. 9, 1979, abandoned.

[51] Int. Cl.³ .................. A61K 31/505; C07D 487/04
[52] U.S. Cl. ..................................... 424/251; 544/281
[58] Field of Search ......................... 544/281; 424/251

[56] References Cited

U.S. PATENT DOCUMENTS

| | | | |
|---|---|---|---|
| 3,157,655 | 11/1964 | Takamizawa et al. | 544/281 |
| 3,907,799 | 9/1975 | O'Brien et al. | 544/281 |
| 3,920,652 | 11/1975 | Springer et al. | 544/281 |
| 3,925,385 | 12/1975 | O'Brien et al. | 544/281 |
| 4,178,449 | 12/1979 | Dusza et al. | 544/281 |

OTHER PUBLICATIONS

Kirkpatrick et al., Chemical Abstracts, vol. 86, 83509x (1977).

*Primary Examiner*—Donald G. Daus
*Assistant Examiner*—Diana G. Rivers

[57] ABSTRACT

This disclosure describes substituted pyrazolo[1,5-a]pyrimidines which possess anxiolytic activity.

18 Claims, No Drawings

SUBSTITUTED PYRAZOLO (1,5-A)PYRIMIDINES AND THEIR USE AS ANXIOLYTIC AGENTS

CROSS REFERENCE TO RELATED APPLICATION

This application is a continuation-in-part of our co-pending application, Ser. No. 55,941, filed July 9, 1979, now abandoned.

BRIEF SUMMARY OF THE INVENTION

This invention relates to new organic compounds and more particularly, is concerned with novel substituted pyrazolo[1,5-a]pyrimidines which may be represented by the following structural formula:

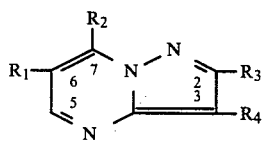

wherein $R_1$ is hydrogen or alkyl having from 1 to 3 carbon atoms; $R_2$ is selected from the group consisting of

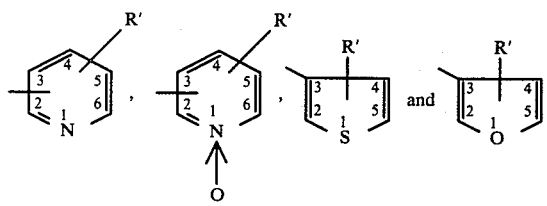

wherein R' is hydrogen or alkyl having from 1 to 3 carbon atoms; $R_3$ is hydrogen, fluoro, chloro, bromo, cyano, cyanomethyl, carbamoyl or alkyl having from 1 to 3 carbon atoms; $R_4$ is selected from the group consisting of hydrogen, fluoro, chloro, bromo, formyl, carboxyl, cyano, hydroxymethyl, N-hydroxyformimidoyl, alkyl having from 1 to 3 carbon atoms and moieties of the formulae:

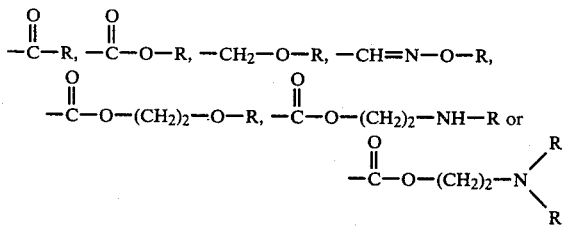

where R is alkyl having from 1 to 3 carbon atoms.

DETAILED DESCRIPTION OF THE INVENTION

The novel compounds of the present invention are obtainable as colorless to yellow crystalline materials having characteristic melting points and absorption spectra. They are appreciably soluble in many organic solvents such as lower alkanols, chloroform, tetrahydrofuran, N,N-dimethylformamide and the like but are generally insoluble in water.

The novel 7-(heteroaryl)pyrazolo[1,5-a]pyrimidines(I) of the present invention may be readily prepared as set forth in the following reaction scheme:

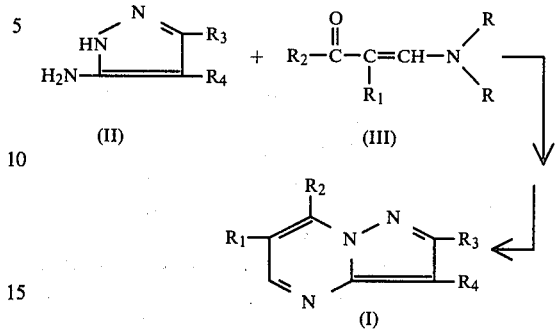

wherein R, $R_1$, $R_2$, $R_3$ and $R_4$ are as hereinabove defined. The reaction of an appropriately substituted 3-aminopyrazole (II) with an appropriately substituted 3-dialkylamino-1-(3-heteroaryl)-2-propen-1-one (III) is best carried out in inert organic solvents such as lower alkanols, dioxane, tetrahydrofuran, toluene and the like at the reflux temperature thereof, and with or without acid catalysis. However, the preferred procedure involves the reaction of (II), with (III) in refluxing glacial acetic acid for a period of 2–24 hours to provide the product (I). The intermediate 3-dialkylamino-1-(heteroaryl)-2-propen-1-ones (III) are readily prepared by the reaction of acetyl, propionyl, or butyryl pyridines, thiophenes, or furans and the like with a dialkylformamide acetal such as dimethylformamide dimethylacetal at 90°–150° C. for 8–24 hours. The 7-(heteroaryl)pyrazolo[1,5-a]pyrimidines (I) wherein $R_4$ is hydrogen, may be readily halogenated with reagents such as chlorine, N-chlorosuccinimide, N-chlorobenzotriazole, bromine, N-bromosuccinimide, and the like to provide the 3-halo derivatives.

The novel 7-(heteroaryl)pyrazolo[1,5-a]-pyrimidines of the present invention may also be readily prepared as set forth in the following reaction scheme:

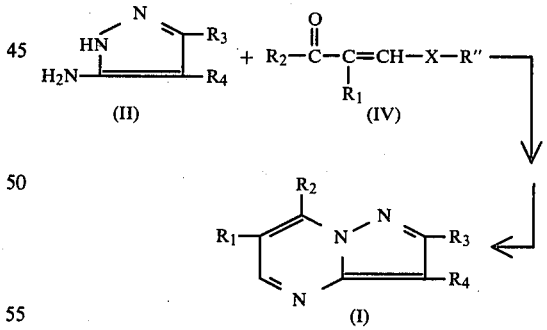

wherein $R_1$, $R_2$, $R_3$ and $R_4$ are as hereinabove defined; R" is hydrogen, alkyl having from 1 to 3 carbon atoms, acetyl, benzoyl, or an alkali metal (e.g., sodium, potassium or lithium) and where X is oxygen or sulfur. The reaction of an appropriately substituted 3-aminopyrazole (II) with an appropriate 3-alkoxy, 3-hydroxy, 3-acetoxy or 3-benzyloxy-1-(heteroaryl)-2-propen-1-one (IV) and the like as well as alkali metal salts thereof is best carried out in inert organic solvents such as lower alkanols, dioxane, tetrahydrofuran, toluene and the like at the reflux temperature thereof and with or without acid catalysis. The reaction is preferably carried out in refluxing glacial acetic acid for a period of 2–24 hours. When R" is an alkali metal such as sodium or potassium, one equivalent of acid is added to give a compound of formula (IV) wherein R" is hydrogen, as an intermediate in the ring closure to compounds of formula (I). Intermediates of formula (IV) where X is oxygen and R" is hydrogen, sodium, potassium or lithium may be prepared by formylation of acetyl, propionyl, or butyrylpyridines, thiophenes, furanes or their substituted forms and the like with lower alkyl formates in the presence of alkaline metal alkoxides. Reaction of compounds of formula (IV) where R" is sodium, potassium or lithium with acetic anhydride gives compounds of formula (IV) where R" is acetyl. The reaction of compounds of formula (IV) where R" is hydrogen, sodium, potassium or lithium with anhydrous acids such as hydrochloric acid and the like in the presence of lower alkanols gives the compounds of formula (IV) where R" is alkyl.

Compounds of formula (I) wherein $R_1$, $R_2$ and $R_3$ are as previously defined and $R_4$ is hydrogen may be prepared by the following reaction scheme:

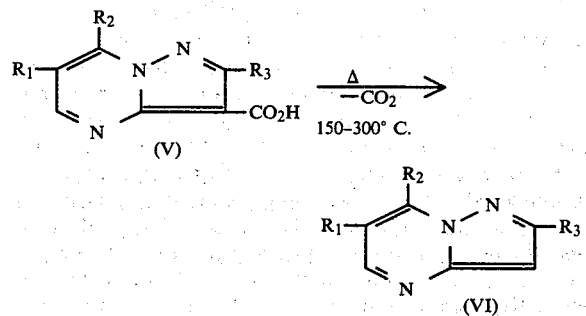

Heating compounds of structure (V) at 250°–300° C. in an inert atmosphere leads to decarboxylation and gives compounds of structure (VI). The novel compounds of formula (I) wherein $R_1$, $R_2$ and $R_3$ are as previously defined and $R_4$ is methyl may be prepared by the following reaction scheme:

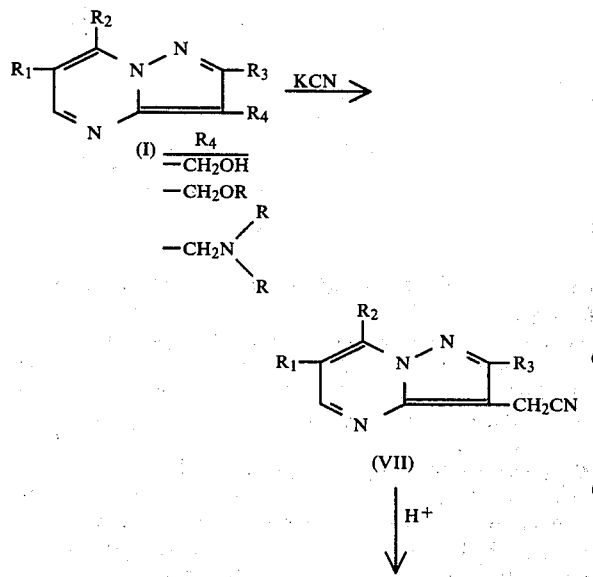

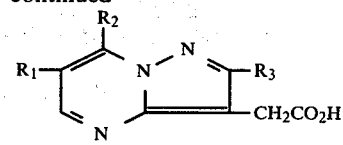

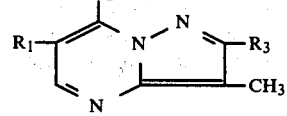

The novel compounds of formula (I) wherein $R_2$ is

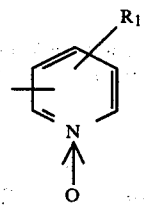

are prepared by reaction of compounds of formula (I) wherein $R_2$ is

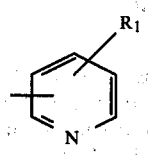

with hydrogen peroxide or peracids such as m-chloroperbenzoic acids to introduce the N-oxide function.

The novel compounds of the present invention possess central nervous system activity at non-toxic doses and as such are useful as anxiolytic agents. That is, they produce certain responses in standard tests with laboratory animals which are known to correlate well with relief of anxiety in man.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, containing 0.5% v/v polyethylene glycol and one drop of Polysorbate 80 to groups of at least 4 rats. At 30 or 60 minutes, the rats were treated intravenously with pentylenetetrazole at a dose of 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E.

Moore, Raven Press, New York, pp. 237–288 (1971)] that there is a high degree of correlation between antagonism of pentylenetetrazole seizures in rats and anti-anxiety effects in higher warm-blooded animals. The following representative compounds of the present invention listed in Table I have been shown to possess anxiolytic activity when tested as described above.

TABLE I

| Protection Against Clonic Seizures Caused By Pentylenetetrazole in Rats | |
|---|---|
| Compound | Result |
| 7-(3-pyridyl)pyrazolo[1,5-a]pyrimidine-3-carbonitrile | active |
| 2-ethyl-7-(3-pyridyl)pyrazolo[1,5-a]pyrimidine-3-carboxylic acid ethyl ester | active |
| 2-ethyl-7-(3-pyridyl)pyrazolo[1,5-a]pyrimidine-3-carbonitrile | active |
| 7-(3-thienyl)pyrazolo[1,5-a]pyrimidine-3-carbonitrile | active |
| 7-(3-thienyl)pyrazolo[1,5-a]pyrimidine-3-carboxylic acid ethyl ester | active |
| 7-(3-pyridyl)pyrazolo[1,5-a]pyrimidine-3-carboxylic acid ethyl ester | active |
| 7-(3-pyridyl)pyrazolo[1,5-a]pyrimidine | active |
| 6-methyl-7-(3-pyridyl)pyrazolo[1,5-a]pyrimidine-3-carbonitrile | active |
| 3-bromo-7-(3-pyridyl)pyrazolo[1,5-a]pyrimidine | active |
| 3-chloro-7-(3-pyridyl)pyrazolo[1,5-a]pyrimidine | active |
| 3-bromo-7-(3-pyridyl)pyrazolo[1,5-a]pyrimidine, pyridine-1-oxide | active |
| 3-bromo-6-methyl-7-(3-pyridyl)pryazolo[1,5-a]pyrimidine | active |
| 7-(3-pyridyl)pyrazolo[1,5-a]pyrimidine, pyridine-1-oxide | active |
| 2-methyl-7-(3-pyridyl)pyrazolo[1,5-a]pyrimidine-3-carbonitrile | active |
| 2,6-dimethyl-7-(3-pyridyl)pyrazolo[1,5-a]pyrimidine-3-carbonitrile | active |
| 2-methyl-7-(3-pyridyl)pyrazolo[1,5-a]pyrimidine-3-carboxylic acid ethyl ester | active |

Another test which has been used to assess anti-anxiety effects is a non-conditioned passive avoidance procedure described by J. R. Vogel, B. Beer and D. E. Clody, "A Simple and Reliable Conflict Procedure for Testing Anti-Anxiety Agents", Psychopharmacologia, 21, 1–7 (1971). A conflict situation is induced in rats by a modification of this method.

Groups of 6 naive, Wistar strain rats, weighing 200–240 g. each were deprived of water for 48 hours and food for 24 hours. The test compounds were administered in single or graded, oral or intraperitoneal doses, suspended in a 2% starch vehicle containing 0.5% v/v polyethylene glycol and one drop of Polysorbate 80. Control animals received the vehicle alone. At 30 or 60 minutes each rat was placed in an individual black plexiglass chamber. A 10% dextrose solution was available ad libitum from a tap located in the rear of the chamber. A 0.3 milliampere DC shocking current was established between the stainless steel grid floor and the tap. After 20 seconds of non-shocked drinking, an alternating 5 second "shock-on" and 5 second "shock-off" cycle began and continued for a total of 5 minutes. The number of shocks taken by each rat during the 5 minute interval was recorded and compared to a control group. The test compounds are considered active if the number of shocks received by the test group is significantly higher than the control group by the Mann-Witney U test. Representative compounds of the present invention which are active when tested by the non-conditioned passive avoidance procedure described above are listed in Table II.

TABLE II

| Non-Conditioned Passive Avoidance Test in Rats | |
|---|---|
| Compound | Results |
| 7-(3-pyridyl)pyrazolo[1,5-a]pyrimidine-3-carbonitrile | active |
| 2-ethyl-7-(3-pyridyl)pyrazolo[1,5-a]pyrimidine-3-carbonitrile | active |

Another test utilized for the determination of anxiolytic activity is the measurement of the ability of test compounds to inhibit the binding of tritiated benzodiazepines to brain-specific receptors of warm-blooded animals. A modification of the method described by R. F. Squires et al. Nature, 266, No. 21, pg. 732, (April, 1977) and H. Mohler et al. Science, 198, pg. 849, (1977) was employed.

Male albino rats (Wistar strain, weighing 150–200 g. each) were obtained from Royalhart Farms. $^3$H-Methyl-diazepam (79.9 Ci/mmol) and $^3$H-methyl-flunitrazepam (84.3 Ci/mmol) were obtained from New England Nuclear. The test compounds were solubilized in either dimethylformamide, acetic acid, ethanol or hydrochloric acid.

Whole cortex of rats was homogenized gently in 20 volumes of ice-cold 0.32 M. sucrose, centrifuged twice at 1000 g of 10 minutes and then recentrifuged at 30,000 g for 20 minutes to produce a crude $P_2$-synaptosomal fraction. The $P_2$-fraction was either: (1) resuspended in twice the original volume in hypotonic 50 mM. Tris.HCl (pH 7.4), or (2) resuspended in one-half the original volume in hypotonic 10 mM. Tris.HCl (pH 7.4) and frozen ($-20°$ C.) until time of use. Frozen $P_2$ preparations were thawed and resuspended in four times the original homogenizing volume at time of assay.

The binding assay consisted of 300 μl. of the $P_2$-fraction suspension (0.2–0.4 mg. protein), 100 μl. of test drug and 100 μl. of $^3$H-diazepam (1.5 nM., final concentration) or $^3$H-flunitrazepam (1.0 nM, final concentration) which was added to 1.5 ml. of 50 mM. Tris.HCl (pH 7.4). Non-specific binding controls and total binding controls received 100 μl. of diazepam (3 μM. final concentration) and 100 μl. of deionized water, respectively, in place of the test compound. Incubation for 30 minutes proceeded in ice and was terminated by filtration, under vacuum, through Whatman GF/C glass fiber filters. The filters were washed twice with 5 ml. of ice-cold 50 mM. Tris.HCl (pH 7.4) and placed in scintillation vials. After drying at 50°–60° C. for 30 minutes, 10 ml. of Beckman Ready-Solve HP was added and the radioactivity determined in a Beckman Scintillation Counter.

Compounds which exhibited the ability to inhibit $^3$H-benzodiazepine binding by 20% were considered to be active. Inhibition of binding was calculated by the difference between total binding and binding in the presence of test compound, divided by the total binding, × 100.

Representative compounds of the present invention which are active when tested by the $^3$H-benzodiazepine binding assay are listed in Table III.

TABLE III

Inhibition of the Binding of $^3$H-Benzodiazepine
Brain-specific Receptors of Rats

| Compound | Result |
| --- | --- |
| 7-(3-pyridyl)pyrazolo[1,5-a]pyrimidine-3-carboxylic acid ethyl ester | active |
| 2-ethyl-7-(3-pyridyl)pyrazolo[1,5-a]pyrimidine-3-carboxylic acid ethyl ester | active |
| 7-(3-thienyl)pyrazolo[1,5-a]pyrimidine-3-carboxylic acid ethyl ester | active |
| 7-(3-pyridyl)pyrazolo[1,5-a]pyrimidine-3-carbonitrile | active |

The novel compounds of the present invention have been found to be highly useful for meliorating anxiety in mammals when administered in amounts ranging from about 0.1 mg. to about 20.0 mg./kg. of body weight per day. A preferred dosage regimen for optimum results would be from about 0.5 mg. to about 10.0 mg./kg. of body weight per day. Such dosage units are employed that a total of from about 35 to about 700 mg. of active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weight of from about 200 to 1500. Although the amount of active compound dissolved in the above vehicle may vary from 0.10% to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

7-(3-Pyridyl)pyrazolo[1,5-a]pyrimidine

A mixture of 50.0 g. of 3-acetylpyridine and 60 ml. of N,N-dimethylformamide dimethylacetal is heated at reflux temperature for 16 hours. The solvent is removed in vacuo and hexane is added to the residue to crystallize a solid. The solid is recrystallized from methylene chloride-hexane to give 36.5 g. of 3-dimethylamino-1-(3-pyridyl)-2-propen-1-one, m.p. 66°–67° C.

A mixture of 8.81 g. of the preceding compound and 4.15 g. of 3-aminopyrazole in 50 ml. of glacial acetic acid is heated at reflux temperature for 8 hours. The solvent is removed in vacuo and the residue is dissolved in dichloromethane. The solution is washed with an aqueous saturated solution of sodium bicarbonate then the organic layer is separated and concentrated. Hexane is added and the mixture is chilled to crystallize a solid. The solid is collected by filtration to give the product of the example as crystals, m.p. 146°–147° C.

EXAMPLE 2

7-(3-Pyridyl)pyrazolo[1,5-a]pyrimidine-3-carbonitrile

A mixture of 17.61 g. of 3-dimethylamino-1-(3-pyridyl)-2-propen-1-one and 10.8 g. of 3-aminopyrazole-4-carbonitrile in 75 ml. of glacial acetic acid is heated at reflux temperature for 6 hours. The procedure described in Example 1 is continued to give the product of the example as tan crystals, m.p. 258°–260° C.

EXAMPLE 3

3-Methyl-7-(3-pyridyl)pyrazolo[1,5-a]pyrimidine

As for Example 2, 3-amino-4-methylpyrazole is heated at reflux temperature for 6 hours with 3-dimethylamino-1-(3-pyridyl)-2-propen-1-one in glacial acetic acid to give the product of the example.

EXAMPLE 4

3-Chloro-7-(3-pyridyl)pyrazolo[1,5-a]pyrimidine

As for Example 2, 3-amino-4-chloropyrazole is heated at reflux temperature for 6 hours with 3-dimethylamino-1-(3-pyridyl)-2-propen-1-one in glacial acetic acid to give the product of the example, m.p. 225°–226° C.

EXAMPLE 5

3-Chloro-7-(6-methyl-3-pyridyl)pyrazolo[1,5-a]pyrimidine

As for Example 1, 3-acetyl-6-methylpyridine is refluxed with N,N-dimethylformamide dimethylacetal to yield 3-dimethylamino-1-(6-methyl-3-pyridyl)-2-propen-1-one. The preceding compound is heated at reflux temperature for 6 hours with 3-amino-4-chloropyrazole in glacial acetic acid to give the product of the example.

EXAMPLE 6

2-Ethyl-7-(3-pyridyl)pyrazolo[1,5-a]pyrimidine-3-carbonitrile

As for Example 2, 2.72 g. of 3-amino-5-ethylpyrazole-4-carbonitrile is heated at reflux temperature for 16 hours with 3.52 g. of 3-dimethylamino-1-(3-pyridyl)-2-propen-1-one in 25 ml. of glacial acetic acid to give 2.65 g. of the product of the example as colorless crystals, m.p. 170°–172° C.

EXAMPLE 7

7-(3-Pyridyl)pyrazolo[1,5-a]-pyrimidine-3-carboxylic acid ethyl ester

As for Example 2, 1.04 g. of 3-amino-4-carboethoxypyrazole is heated at reflux temperature for 16 hours with 1.18 g. of 3-dimethylamino-1-(3-pyridyl)-2-propen-1-one in 25 ml. of glacial acetic acid to give 1.30 g. of the product of the example as colorless needles, m.p. 170°–171° C.

EXAMPLE 8

2-Ethyl-7-(3-pyridyl)pyrazolo[1,5-a]pyrimidine-3-carboxylic acid ethyl ester As for Example 2, 1.83 g. of 3-amino-4-carboethoxy-5-ethylpyrazole is heated at reflux temperature for 16 hours with 1.76 g. of 3-dimethylamino-1-(3-pyridyl)-2-propen-1-one in 25 ml. of glacial acetic acid to give 1.20 g. of the product of the example as colorless crystals, m.p. 119°–120° C.

EXAMPLE 9

7-(3-Thienyl)pyrazolo[1,5-a]pyrimidine-3-carboxylic acid ethyl ester

As for Example 2, 3.10 g. of 3-amino-4-carboethoxypyrazole is heated at reflux temperature for 10 hours with 3.62 g. of 3-dimethylamino-1-(3-thienyl)-2-propen-1-one in 25 ml. of glacial acetic acid to give 4.40 g. of the product of the example as tan crystals, m.p. 129°–130° C.

EXAMPLE 10

7-(3-Thienyl)pyrazolo[1,5-a]pyrimidine-3-carbonitrile

As for Example 1, 35.0 g. of 3-acetylthiophene is heated at reflux temperature for 12 hours with 50 ml. of N,N-dimethylformamide dimethylacetal to yield 43.5 g. of crude product. A 5.0 g. portion of this material is recrystallized from methylene chloride-hexane to yield 3.85 g. of 3-dimethylamino-1-(3-thienyl)-2-propen-1-one, m.p. 89°–90° C.

A 3.24 g. amount of 3-aminopyrazole-4-carbonitrile is heated at reflux temperature for 16 hours with 5.44 g. of the preceding product in 25 ml. of glacial acetic acid to give 3.25 g. of the product of the example as colorless crystals, m.p. 215°–216° C.

EXAMPLE 11

6-Methyl-7-(3-pyridyl)pyrazolo[1,5-a]pyrimidine-3-carbonitrile

A mixture of 50.0 g. of 3-propionylpyridine and 55 ml. of N,N-dimethylformamide dimethylacetal is heated at reflux temperature for 15 hours. The solvent is removed in vacuo and the residue is crystallized on cooling. The solid is dissolved in methylene chloride and the solution is passed through a column of hydrous magnesium silicate. The addition of hexane to the eluent provides 34.4 g. of 3-dimethylamino-2-methyl-1-(3-pyridyl)-2-propen-1-one as pale yellow crystals, m.p. 76°–78° C.

A mixture of 5.70 g. of the preceding product and 3.24 g. of 3-aminopyrazole-4-carbonitrile in 25 ml. of glacial acetic acid is heated at reflux temperature for 15 hours. The solvent is removed in vacuo.

The residue is treated with a saturated aqueous solution of sodium bicarbonate and extracted with methylene chloride. The organic layer is dried over anhydrous sodium sulfate and passed through a column of hydrous magnesium silicate. The addition of hexane to the eluate separates 4.00 g. of the product of the example as colorless crystals, m.p. 193.5°–194.5° C.

EXAMPLE 12

7-(3-Pyridyl)pyrazolo[1,5-a]-pyrimidine-3-carboxaldehyde

A 1.0 g. sample of 7-(3-pyridyl)pyrazolo[1,5-a]-pyrimidine is added to an ice cold solution of 1.0 ml. of phosphorus oxychloride in 3 ml. of N,N-dimethylformamide. The reaction mixture is heated on a steam bath for 3 hours and poured into ice. The mixture is made basic with a solution of sodium hydroxide and extracted into dichloromethane. The dichloromethane solution is washed with water and passed through a column of hydrous magnesium silicate. The eluent is concentrated and diluted with hexane to give the product of the example as crystals.

EXAMPLE 13

7-(3-Pyridyl)pyrazolo[1,5-a]pyrimidine-3-carbonitrile

A mixture of 0.01 mole of 7-(3-pyridyl)pyrazolo-[1,5-a]pyrimidine-3-carboxaldehyde and 0.011 mole of hydroxylamine hydrochloride in 25 ml. of ethanol is heated on a steam bath for 3 hours. The solvent is removed and to the residue is added 25 ml. of acetic anhydride. The mixture is heated at reflux temperature for 6 hours and the solvent is removed in vacuo. The residue is partitioned between dichloromethane and sodium bicarbonate solution and the organic layer is separated, dried over magnesium sulfate, and the solvent removed to give the product of the example, m.p. 258°–260° C.

EXAMPLE 14

7-(3-Pyridyl)pyrazolo[1,5-a]pyrimidine-3-methanol

A mixture of 0.10 mole of 7-(3-pyridyl)pyrazolo-[1,5-a]pyrimidine-3-carbonitrile and concentrated hydrochloric acid in acetic acid is heated at reflux temperature for 16 hours. The solvent is removed to give 7-(3-pyridyl)-pyrazolo[1,5-a]pyrimidine-3-carboxylate hydrochloride. The preceding compound is added portionwise to a chilled solution of 0.30 mole of diborane in tetrahydrofuran. After the addition the mixture is stirred for 16 hours and poured onto ice to give the product of the example.

EXAMPLE 15

7-(3-Pyridyl)pyrazolo[1,5-a]pyrimidine-3-methanol

A mixture of 0.10 mole of ethyl 7-(3-pyridyl)-pyrazolo[1,5-a]pyrimidine-3-carboxylate and 0.50 mole of potassium hydroxide in 50 ml. of ethanol-water (9:1) is heated at reflux temperature for 4 hours. The mixture is brought to pH 7 with concentrated hydrochloric acid, concentrated and filtered to give 7-(3-pyridyl)-pyrazolo[1,5-a]pyrimidine-3-carboxylic acid. The preceding product in tetrahydrofuran is added dropwise to a solution of 0.2 mole of diborane in tetrahydrofuran chilled in an ice bath. The mixture is stirred for one hour and the bath removed. After standing 16 hours at room temperature the mixture is poured onto ice to give the product of the example.

EXAMPLE 16

7-(3-Thienyl)pyrazolo[1,5-a]pyrimidine-3-methanol

A mixture of 0.05 mole of ethyl 7-(3-thienyl)-pyrazolo[1,5-a]pyrimidine-3-carboxylate and 0.20 mole of potassium hydroxide in 50 ml. of ethanol-water is heated at reflux temperature for 4 hours. The mixture is acidified with concentrated hydrochloric acid and concentrated to give 7-(3-thienyl)pyrazolo[1,5-a]pyrimidine-3-carboxylic acid. The preceding compound in tetrahydrofuran is added dropwise to a solution of 0.10 mole of diborane in tetrahydrofuran chilled in an ice bath. After stirring for 2 hours the bath is removed and the mixture allowed to stand 6 hours at room temperature. The mixture is poured into ice to give the product of the example.

EXAMPLE 17

7-(3-Furyl)pyrazolo[1,5-a]pyrimidine

A mixture of 50.0 g. of 3-acetylfuran and 60 ml. of N,N-dimethylformamide is heated at reflux temperature for 16 hours. The solvent is removed in vacuo and hexane is added to the residue to give 3-dimethylamino-1-(3-furyl)-2-propen-1-one. A mixture of 0.01 mole of the preceding compound and 0.01 mole of 3-aminopyrazole in glacial acetic acid is refluxed for 8 hours and the solvent removed in vacuo. The residue is purified as described in Example 1 to give the product of the example.

EXAMPLE 18

7-(3-Furyl)pyrazolo[1,5-a]pyrimidine-3-carbonitrile

A mixture of 0.01 mole of 3-dimethylamino-1-(3-furyl)-2-propen-1-one and 0.01 mole of 3-aminopyrazole-4-carbonitrile in glacial acetic acid is heated at reflux temperature for 6 hours. The solvent is removed in vacuo and the residue purified as described for Example 1 to give the product of the example.

EXAMPLE 19

Ethyl 7-(3-Furyl)pyrazolo[1,5-a]pyrimidine-3-carboxylate

A mixture of 0.01 mole of 3-dimethylamino-1-(3-furyl)-2-propen-1-one and 0.01 mole of ethyl 3-aminopyrazole-4-carboxylate in glacial acetic acid is heated at reflux temperature for 6 hours. The product is isolated as described for Example 1 to give the product of the example.

EXAMPLE 20

7-(3-Furyl)pyrazolo[1,5-a]pyrimidine-3-methanol

As described for Example 15 7-(3-furyl)pyrazolo-[1,5-a]pyrimidine-3-carboxylic acid is reduced with diborane to give the product of the example.

EXAMPLE 21

7-(3-Pyridyl)pyrazolo[1,5-a]pyrimidine-3-methanol

A mixture of 2.0 g. of 7-(3-pyridyl)pyrazolo[1,5-a]-pyrimidine-3-carboxaldehyde and 0.35 g. of sodium borohydride in 100 ml. of methanol is stirred for 16 hours. The mixture is concentrated to dryness in vacuo and dichloromethane is added. The solution is washed with saturated sodium bicarbonate and passed through a column of hydrous magnesium silicate. The eluent is concentrated and diluted with hexane to give the product of the example.

EXAMPLE 22

7-(3-Pyridyl)pyrazolo[1,5-a]pyrimidine-3-carbonitrile

A mixture of 1.0 g. of 3-bromo-7-(3-pyridyl)-pyrazolo[1,5-a]pyrimidine and 0.50 g. of cuprous cyanide in 25 ml. of N,N-dimethylformamide is heated at reflux temperature for 16 hours. The solvent is removed in vacuo and the residue is triturated with dichloromethane. The dichloromethane solution is passed through a column of hydrous magnesium silicate. The eluent is concentrated and hexane added to give the product of the example as tan crystals, m.p. 258°–260° C.

EXAMPLE 23

7-(3-Pyridyl)pyrazolo[1,5-a]pyrimidine-3-carbonitrile

A mixture of 1.0 g. of 7-(3-pyridyl)pyrazolo[1,5-a]-pyrimidine-3-carboxamide and 5 ml. of phosphorus oxychloride is heated at reflux temperature for 3 hours. The mixture is concentrated to dryness in vacuo. The residue is dissolved in dichloromethane and washed with a saturated solution of sodium bicarbonate. The dichloromethane solution is dried over magnesium sulfate and passed through a column of hydrous magnesium silicate. The eluent is concentrated and diluted with hexane to give the product of the example as crystals, m.p. 258°–260° C.

EXAMPLE 24

3-Bromo-7-(3-pyridyl)pyrazolo[1,5-a]pyrimidine

A mixture of 1.96 g. of 7-(3-pyridyl)pyrazolo[1,5-a]pyrimidine and 1.97 g. of N-bromosuccinimide in 100 ml. of dichloromethane is heated on a steam bath for 15 minutes. The mixture is poured into ice cold 2.5 N sodium hydroxide. The organic layer is separated and dried then is passed through a column of hydrous magnesium silicate. The column is washed with dichloromethane and the eluent is concentrated and diluted with hexane to give 1.8 g. of the product of the example, m.p. 243°–244° C.

EXAMPLE 25

3-Bromo-7-(3-pyridyl)pyrazolo[1,5-a]pyrimidine

A mixture of 0.01 mole of 3-dimethylamino-1-(3-pyridyl)-2-propen-1-one and 0.01 mole of 3-amino-4-bromopyrazole in glacial acetic acid is heated at reflux temperature for 8 hours. The solvent is removed to give the product of the example, m.p. 243°–244° C.

EXAMPLE 26

3-Bromo-7-(3-thienyl)pyrazolo[1,5-a]pyrimidine

A mixture of 0.01 mole of 3-dimethylamino-1-(3-thienyl)-2-propen-1-one and 0.01 mole of 3-amino-4-bromopyrazole in glacial acetic acid is heated at reflux temperature for 8 hours. The solvent is removed in vacuo to give the product of the example.

EXAMPLE 27

3-Bromo-7-(3-furyl)pyrazolo[1,5-a]pyrimidine

A mixture of 0.01 mole of 3-dimethylamino-1-(3-furyl)-2-propen-1-one and 0.01 mole of 3-amino-4-bromopyrazole in glacial acetic acid is heated at reflux temperature for 6 hours. The solvent is removed to give the product of the example.

EXAMPLE 28

3-Methyl-7-(3-thienyl)pyrazolo[1,5-a]pyrimidine

A mixture of 0.01 mole of 3-dimethylamino-1-(3-thienyl)-2-propen-1-one and 0.01 mole of 3-amino-4-methylpyrazole in glacial acetic acid is heated at reflux temperature for 8 hours. The solvent is removed in vacuo to give the product of the example.

EXAMPLE 29

3-Methyl-7-(3-furyl)pyrazolo[1,5-a]pyrimidine

A mixture of 0.01 mole of 3-dimethylamino-1-(3-furyl)-2-propen-1-one and 3-amino-4-methylpyrazole in glacial acetic acid is heated at reflux temperature for 6 hours. The solvent is removed to give the product of the example.

EXAMPLE 30

3-(Methoxymethyl)-7-(3-pyridyl)pyrazolo[1,5-a]pyrimidine

To a mixture of 0.01 mole of 7-(3-pyridyl)pyrazolo-[1,5-a]pyrimidine-3-methanol in 50 ml. of methanol is added anhydrous hydrochloric acid in 10 ml. of methanol. The mixture is heated on a steam bath for 3 hours and the solvent removed. The residue is partitioned between dichloromethane and aqueous sodium bicarbonate. The dichloromethane solution is dried over magnesium sulfate, concentrated and diluted with hexane to give the product of the example.

EXAMPLE 31

3-(Ethoxymethyl)-7-(3-pyridyl)pyrazolo[1,5-a]pyrimidine

A mixture of 0.01 mole of ethyl 7-(3-pyridyl)-pyrazolo[1,5-a]pyrimidine-3-carboxylate and lithium aluminum hydride in ether is heated at reflux temperature for 8 hours. To the mixture is added (dropwise) ethanol and water. The ethereal layer is separated, then ethanol and anhydrous hydrochloric acid is added to it. The resulting mixture is refluxed for 8 hours and the solvent is removed. The residue is extracted with dichloromethane. The dichloromethane extract is passed through a column of hydrous magnesium silicate. The eluent is concentrated and diluted with hexane to give the product of the example.

EXAMPLE 32

Methyl 7-(3-pyridyl)pyrazolo[1,5-a]pyrimid-3-yl ketone

An ether solution of 0.002 mole of methyl magnesium iodide is prepared from methyl iodide and magnesium. A slurry of 7-(3-pyridyl)pyrazolo[1,5-a]pyrimidine-3-carboxaldehyde in 100 ml. of anhydrous ether is added and the mixture is heated at reflux temperature for 3 hours. After cooling, water is added and the mixture is acidified with 1 N hydrochloric acid. The organic layer is separated, and the solvent evaporated to give α-methyl-7-(3-pyridyl)pyrazolo[1,5-a]-pyrimidine-3-methanol. A 3.0 g. amount of the preceding compound and 1.0 g. of chromium trioxide in 75 ml. of glacial acetic acid is stirred at room temperature for one hour then is poured into water to give the product of the example.

EXAMPLE 33

3-Methyl-7-(3-pyridyl)pyrazolo[1,5-a]pyrimidine

A mixture of 0.01 mole of 7-(3-pyridyl)pyrazolo-[1,5-a]pyrimidine-3-methanol and 0.025 mole of potassium cyanide in N,N-dimethylformamide is heated at 100° C. for 16 hours. The solvent is removed and water is added to the residue to give 7-(3-pyridyl)pyrazolo[1,5-a]pyrimidine-3-acetonitrile. A mixture of 0.001 mole of the preceding compound in a 1:1 mixture of acetic acid and concentrated hydrochloric acid is heated at reflux temperature for 16 hours. The solvent is removed to give 7-(3-pyridyl)pyrazolo[1,5-a]pyrimidine-3-acetic acid. The preceding compound is heated at 180° C. to give the product of the example.

EXAMPLE 34

3-Chloro-7-(3-pyridyl)pyrazolo[1,5-a]pyrimidine

A mixture of 3.92 g. of 7-(3-pyridyl)pyrazolo[1,5-a]-pyrimidine and 3.40 g. of N-chlorobenzotriazole in 100 ml. of dichloromethane is heated on a steam bath for 15 minutes. The mixture is poured into 100 ml. of ice cold 2.5 N sodium hydroxide and the dichloromethane layer is separated and dried over anhydrous sodium sulfate. The dichloromethane extract is passed through a column of hydrous magnesium silicate and the eluent is concentrated and diluted with hexane to give 2.75 g. of the product of the example, m.p. 225°–226° C.

EXAMPLE 35

3-Bromo-7-(3-pyridyl)pyrazolo-[1,5-a]pyrimidine pyridine-1-oxide

A mixture of 0.90 g. of 3-bromo-7-(3-pyridyl)-pyrazolo[1,5-a]pyrimidine, 25 ml. of glacial acetic acid and 5 ml. of 30% hydrogen peroxide is heated on a steam bath for 4 hours. The mixture is filtered and the solid recrystallized from ethanol to give 0.40 g. of the product of the example, m.p. 280°–284° C.

EXAMPLE 36

3-Bromo-6-methyl-7-(3-pyridyl)pyrazolo[1,5-a]pyrimidine

A mixture of 1.65 g. of 6-methyl-7-(3-pyridyl)-pyrazolo[1,5-a]pyrimidine and 1.54 g. of N-bromosuccinimide in 50 ml. of dichloromethane is heated on a steam bath for 15 minutes. The mixture is poured into 100 ml. of ice cold 2.5 N sodium hydroxide. The dichloromethane layer is separated, dried over anhydrous sodium sulfate and passed through a column of hydrous magnesium silicate. The eluent is concentrated and hexane added to give 1.20 g. of the product of the example, m.p. 166°–168° C.

EXAMPLE 37

7-(3-Pyridyl)pyrazolo[1,5-a]pyrimidine-3-carbonitrile pyridine-1-oxide

A mixture of 4.42 g of 7-(3-pyridyl)pyrazolo[1,5-a]pyrimidine-3-carbonitrile, 50 ml. of glacial acetic acid and 5 ml. of 30% hydrogen peroxide is heated on a steam bath for 2 hours. The mixture is cooled, filtered and the solid recrystallized from acetic acid to give 2.05 g. of the product of the example, m.p. 294°–295° C.

EXAMPLE 38

7-(3-Pyridyl)pyrazolo[1,5-a]pyrimidine pyridine-1-oxide

A mixture of 1.96 g. of 7-(3-pyridyl)pyrazolo[1,5-a]pyrimidine, 25 ml. of glacial acetic acid and 2 ml. of 30% hydrogen peroxide is heated on a steam bath for 2 hours. The solvent is removed and the residue crystallized from ethanol to give 0.85 g. of the product of the example, m.p. 223°–226° C.

EXAMPLE 39

2-Methyl-7-(3-pyridyl)pyrazolo[1,5-a]pyrimidine-3-carbonitrile

A mixture of 3.50 g. of 3-dimethylamino-1-(3-pyridyl)-2-propen-1-one, 25 ml. of glacial acetic acid and 2.44 g. of 3-amino-5-methylpyrazole-4-carbonitrile is refluxed 6 hours. The solvent is removed in vacuo. The residue is dissolved in dichloromethane and the solution washed with saturated sodium bicarbonate solution. The dichloromethane layer is dried over anhydrous sodium sulfate and pased through a column of hydrous magnesium silicate. The eluent is concentrated and hexane added to give 2.60 g. of the product of the example, m.p. 245°–246° C.

EXAMPLE 40

2,6-Dimethyl-7-(3-pyridyl)pyrazolo[1,5-a]pyrimidine-3-carbonitrile

A mixture of 1.90 g. of 3-dimethylamino-2-methyl-1-(3-pyridyl)-2-propen-1-one and 1.22 g. of 3-amino-5-methylpyrazole-4-carbonitrile in 25 ml. of glacial acetic acid is refluxed for 6 hours. The solvent is removed in vacuo and the residue partitioned between dichloromethane and saturated sodium bicarbonate solution. The dichloromethane layer is separated, dried over anhydrous sodium sulfate and passed through a column of hydrous magnesium silicate. The eluent is concentrated and hexane added to give 0.95 g. of the product of the example, m.p. 207°–209° C.

EXAMPLE 41

2-Methyl-7-(3-pyridyl)pyrazolo[1,5-a]pyrimidine-3-carboxylic acid ethyl ester

A mixture of 9.09 g. of 3-dimethylamino-1-(3-pyridyl)-2-propen-1-one and 2.54 g. of ethyl 3-amino-5-methylpyrazole-4-carboxylate in 25 ml. of glacial acetic acid is refluxed for 16 hours. The solvent is removed and the residue in dichloromethane is washed with saturated sodium bicarbonate solution. The dichloromethane solution is passed through a column of hydrous magnesium silicate. The eluent is concentrated and hexane added to give 3.1 g. of the product of the example, m.p. 145°–146° C.

EXAMPLE 42

7-(3-Pyridyl)pyrazolo[1,5-a]pyrimidine-3-carboxylic acid

A mixture of 6.0 g. of ethyl 7-(3-pyridyl)pyrazolo[1,5-a]pyrimidine-3-carboxylate, 125 ml. of ethanol and 50 ml. of 1 N sodium hydroxide is heated on a steam bath for 4 hours. The mixture is chilled and filtered to give 5.85 g. of sodium 7-(3-pyridyl)pyrazolo[1,5-a]pyrimidine-3-carboxylate, m.p. 360°–363° C. dec. The preceding compound is stirred with 1 N hydrochloric acid and the mixture is filtered to give 5.0 g. of the product of the example, m.p. 286°–287° C. dec. (gas evolution).

EXAMPLE 43

2-Methyl-7-(3-pyridyl)pyrazolo[1,5-]pyrimidine-3-carboxylic acid hydrochloride

A mixture of 3.0 g. of ethyl 2-methyl-7-(3-pyridyl)-pyrazolo[1,5-a]pyrimidine-3-carboxylate, ethanol and 1 N sodium hydroxide is heated on a steam bath as for Example 42 to give 2.92 g. of sodium 2-methyl-7-(3-pyridyl)pyrazolo[1,5-a]pyrimidine-3-carboxylate, m.p. 375°–380° C. dec. A 1.87 g. portion of the preceding compound is stirred for 16 hours with 30 ml. of 1 N hydrochloric acid to give 1.6 g. of the product of the example, m.p. 280° C. dec.

EXAMPLE 44

2-Ethyl-7-(3-pyridyl)pyrazolo[1,5-a]pyrimidine-3-carboxylic acid

A mixture of 9.15 g. of ethyl 2-ethyl-7-(3-pyridyl)-pyrazolo[1,5-a]pyrimidine-3-carboxylate, 100 ml. of ethanol and 60 ml. of 1 N sodium hydroxide is heated on a steam bath for 4 hours. The mixture is chilled and filtered. The collected solid is stirred with 50 ml. of water and 55 ml. of 1 N hydrochloric acid for 16 hours to give 8.0 g. of the product of the example, m.p. 242°–243° C.

EXAMPLE 45

2-Methyl-7-(3-pyridyl)pyrazolo[1,5-a]pyrimidine

A 1.0 g. amount of 2-methyl-7-(3-pyridyl)-pyrazolo[1,5-a]pyrimidine-3-carboxylic acid is heated in an oil bath at 280° C. for 10-20 minutes or until gas evolution ceases, to give the product of the example, m.p. 181.5°-183.5° C.

EXAMPLE 46

2-Ethyl-7-(3-pyridyl)pyrazolo[1,5-a]pyrimidine

As for Example 45, 6.0 g. of 2-ethyl-7-(3-pyridyl)-pyrazolo[1,5-a]pyrimidine-3-carboxylic acid is heated at 280° C. to give the product of the example, m.p. 103°-104° C.

EXAMPLE 47

3-Chloro-2-methyl-7-(3-pyridyl)pyrazolo[1,5-a]pyrimidine

As for Example 34, 2-methyl-7-(3-pyridyl)-pyrazolo[1,5-a]pyrimidine is reacted with N-chlorobenzotriazole to give the product of the example.

EXAMPLE 48

3-Chloro-2-ethyl-7-(3-pyridyl)pyrazolo[1,5-a]pyrimidine

As for Example 34, 1.95 g. of 2-ethyl-7-(3-pyridyl)-pyrazolo[1,5-a]pyrimidine is reacted with 1.47 g. of N-chlorobenzotriazole in 50 ml. of dichloromethane to give the product of the example, m.p. 132°-133° C.

EXAMPLE 49

7-(3-Pyridyl)pyrazolo[1,5-a]pyrimidine-3-carboxaldehyde, oxime

A mixture of 2.0 g. of 7-(3-pyridyl)pyrazolo[1,5-a]pyrimidine-3-carboxaldehyde, 0.50 g. of hydroxylamine hydrochloride and 0.9 g. of sodium acetate in 50 ml. of ethanol is heated on a steam bath to give the product of the example.

EXAMPLE 50

7-(3-Pyridyl)pyrazolo[1,5-a]pyrimidine-3-carbonitrile

A mixture of 1.0 g. of 3-bromo-7-(3-pyridyl)-pyrazolo[1,5-a]pyrimidine, 0.45 g. of cuprous cyanide and 25 ml. of N,N-dimethylformamide is refluxed for 16 hours. The solvent is removed and the residue triturated with dichloromethane. The dichloromethane extract is passed through a column of hydrous magnesium silicate. The eluent is concentrated and hexane added to give the product of the example, m.p. 258°-260° C.

EXAMPLE 51

2-Dimethylaminoethyl 7-(3-pyridyl)pyrazolo[1,5-a]pyrimidine-3-carboxylate

To a mixture of ethyl 7-(3-pyridyl)pyrazolo[1,5-a]pyrimidine-3-carboxylate in 2-dimethylamino ethanol is added sodium hydride. After the hydride is reacted the mixture is heated on a steam bath for 6 hours. The solvent is removed and the residue acidified with dilute acetic acid to give the product of the example.

EXAMPLE 52

2-Ethoxyethyl 7-(3-pyridyl)pyrazolo[1,5-a]pyrimidine-3-carboxylate

To a mixture of ethyl 7-(3-pyridyl)pyrazolo[1,5-a]pyrimidine-3-carboxylate and 2-ethoxyethanol is added sodium hydride. After the hydride is reacted, the mixture is heated on a steam bath for 12 hours. The solvent is removed and the residue is acidified with dilute acetic acid to give the product of the example.

EXAMPLE 53

7-(6-Methyl-2-pyridyl)pyrazolo[1,5-a]pyrimidine-3-carbonitrile

A mixture of 25.0 g of 2-acetyl-6-methylpyridine and 35 ml. of N,N-dimethylformamide dimethylacetal is refluxed for 16 hours. The mixture is cooled and filtered to give 3-dimethylamino-1-(6-methyl-2-pyridyl)-2-propen-1-one as crystals, m.p. 97°-98° C.

The preceding compound (3,80 g.) and 2.16 g. of 3-aminopyrazole-4-carbonitrile in 25 ml. of glacial acetic acid is refluxed for 8 hours. The solvent is removed and the residue dissolved in dichloromethane. The solution is washed with sodium bicarbonate solution and dried (Na$_2$SO$_4$). The solution is passed through a short column of hydrous magnesium silicate. The eluent is concentrated while adding hexane until crystals separate. The mixture is cooled and filtered to give the product of the example, m.p. 225°-226° C.

EXAMPLE 54

7-(6-Methyl-2-pyridyl)pyrazolo[1,5-a]pyrimidine

A mixture of 0.84 g. of 3-aminopyrazole and 1.90 g. of 3-dimethylamino-1-(6-methyl-2-pyridyl)-2-propen-1-one and 25. ml. of glacial acetic acid is heated on a steam bath for 4 hours. The solvent was removed under reduced pressure. The residue is dissolved in dichloromethane and the solution passed through a short column of hydrous magnesium silicate. The element is concentrated and diluted with hexane to give 1.15 g. of crystals, m.p. 126°-127° C.

EXAMPLE 55

Ethyl 7-(6-methyl-2-pyridyl)pyrazolo[1,5-a]pyrimidine-3-carboxylate

A mixture of 3.80 g. of 3-dimethyl-1-(6-methyl-2-pyridyl)-2-propen-1-one and 3.10 g. of ethyl 3-aminopyrazole-4-carboxylate in 25 ml. of glacial acetic acid is refluxed for 16 hours. The solvent is removed under reduced pressure and the residue worked up as for Example 53 to give crystals, m.p. 135°-137° C.

EXAMPLE 56

3-Methyl-7-(6-methyl-2-pyridyl)pyrazolo[1,5-a]pyrimidine

As for example 53, a mixture of 3-dimethylamino-1-(6-methyl-2-pyridyl)-2-propen-1-one and 3-amino-4-methylpyrazole in glacial acetic is refluxed for 4 hours to give the product of the example.

EXAMPLE 57

Ethyl 7-(5-methyl-2-pyridyl)pyrazolo[1,5-a]pyrimidine-3-carboxylate

A mixture of 0.01 mole of 3-dimethylamino-1-(5-methyl-2-pyridyl)-2-propen-1-one and 0.01 mole of ethyl 3-aminopyrazole-4-carboxylate in glacial acetic acid is refluxed for 6 hours. The solvent is removed under reduced pressure and the residue worked up as for Example 53 to give the product of the example.

EXAMPLE 58

7-(5-Methyl-2-pyridyl)pyrazolo[1,5-a]pyrimidine

A mixture of 0.01 mole of 3-dimethylamino-1-(5-methyl-2-pyridyl)-2-propen-1-one and 0.01 mole of 3-aminopyrazole in glacial acetic acid is refluxed for 8 hours and worked up as for Example 53 to give the product of the example.

EXAMPLE 59

7-(4-Methyl-2-pyridyl)pyrazolo[1,5-a]pyrimidine-3-carbonitrile

A mixture of 0.01 mole of 3-dimethylamino-1-(4-methyl-2-pyridyl)-2-propen-1-one and 0.01 mole of 3-aminopyrazole-4-carbonitrile in glacial acetic acid is refluxed for 8 hours and worked up as for Example 53 to give the product of the example.

EXAMPLE 60

7-(5-Methyl-2-pyridyl)pyrazolo[1,5-a]pyrimidine-3-carbonitrile

A mixture of 0.01 mole of 3-dimethylamino-1-(5-methyl-2-pyridyl)-2-propen-1-one and 0.01 mole of 3-aminopyrazole-4-carbonitrile in glacial acetic acid is refluxed for 8 hours and worked up as for Example 53 to give the product of the example.

EXAMPLE 61

7-(2-Pyridyl)pyrazolo[1,5-a]pyrimidine

A mixture of 25 g. of 2-acetylpyridine and 35 ml. of N,N-dimethylformamide dimethylacetal is refluxed for 16 hours. The mixture is cooled and filtered to give 3-dimethylamino-1-(2-pyridyl)-2-propen-1-one as crystals, m.p. 127°–130° C.

A mixture of 0.01 mole of the preceding compound and 0.01 mole of 3-aminopyrazole in glacial acetic acid is refluxed for 8 hours and worked up as for Example 53 to give crystals, m.p. 84°–87° C.

EXAMPLE 62

3-Chloro-7-(2-pyridyl)pyrazolo[1,5-a]pyrimidine

A solution of 0.01 mole of 7-(2-pyridyl)pyrazolo[1,5a]pyrimidine in dichloromethane is cooled and 0.01 mole of N-chlorobenzotriazole is added. After standing at room temperature the mixture is heated on a steam bath for 15 minutes. The warm solution is poured into ice cold 2.5 N sodium hydroxide solution. The organic layer is dried (Na$_2$SO$_4$) and the solution passed through a short column of hydrous magnesium silicate. The eluent is concentrated and diluted with hexane to give the product of the example as crystals, m.p. 141°–143° C.

EXAMPLE 63

7-(4-Pyridyl)pyrazolo[1,5-a]pyrimidine

A mixture of 25 g. of 4-acetylpyridine and 35 ml. of N,N-dimethylformamide dimethylacetyl is refluxed for 16 hours. The mixture is concentrated under reduced pressure and hexane added to the residue to give 3-dimethylamino-1-(4-pyridyl)-2-propen-1-one as crystals, m.p. 114°–116° C.

The preceding compound (0.01 mole) and 0.01 mole of 3-aminopyrazole in glacial acetic acid is refluxed for 8 hours. The solvent is removed under reduced pressure and the product worked up as for Example 53 to give the product of the example as crystals, m.p. 159°–161° C.

EXAMPLE 64

7-(4-Pyridyl)pyrazolo[1,5-a]pyrimidine-3-carbonitrile

A mixture of 1.12 g. of 3-dimethylamino-1-(4-pyridyl)-2-propen-1-one and 0.69 g. of 3-aminopyrazole-4-carbonitrile in 25 ml. of glacial acetic acid is refluxed 6 hours. The solvent is removed under reduced pressure and the product worked up as for Example 53 to give 0.60 g. of crystals, m.p. 137°–138° C.

EXAMPLE 65

Ethyl 7-(4-pyridyl)pyrazolo[1,5-a]pyrimidine-3-carboxylate

A mixture of 3.52 g. of 3-dimethylamino-1-(4-pyridyl)-2-propen-1-one and 3.10 g. of ethyl 3-aminopyrazole-4-carboxylate in 50 ml. of glacial acetic acid is refluxed for 15 hours. The solvent is removed and the residue worked up as for Example 53 to give 3.0 g. of crystals, m.p. 209°–210° C.

EXAMPLE 66

Ethyl 7-(2-pyridyl)pyrazolo[1,5-a]pyrimidine-3-3-carboxylate

A mixture of 1.70 g. of 3-dimethylamino-1-(2-pyridyl)-2-propen-1-one and 1.50 g. of ethyl 3-aminopyrazole-4-carboxylate in 25 ml. of glacial acetic acid is refluxed for 18 hours. The solvent is removed and the product worked up as for Example 53 to give 1.80 g. of crystals, m.p. 153°–154° C.

EXAMPLE 67

3-Chloro-7-(4-pyridyl)pyrazolo[1,5-a]pyrimidine

To a mixture of 0.01 mole of 7-(4-pyridyl)-pyrazolo[1,5-a]pyrimidine in cold dichloromethane is added 0.011 mole of N-chlorobenzotriazole. The mixture is stirred at room temperature for one hour and heated on a steam bath for 15 minutes. The product is worked up as for Example 62 to give the product of the example, m.p. 183°–184° C.

EXAMPLE 68

7-(4-Pyridyl)pyrazolo[1,5-a]pyrimidine-3-carbonitrile, pyridine-1-oxide

A mixture of 4.42 g. of 7-(4-pyridyl)pyrazolo[1,5-a]pyrimidine-3-carbonitrile, 50 ml. of glacial acetic acid and 5 ml. of 30% hydrogen peroxide is heated on a steam bath for 2 hours. The mixture is concentrated, cooled and filtered to give the product of the example.

EXAMPLE 69

3-Chloro-7-(4-pyridyl)pyrazolo[1,5-]pyrimidine, pyridine-1-oxide

A mixture of 0.01 mole of 3-chloro-7-(4-pyridyl)-pyrazolo[1,5-a]pyrimidine in 50 ml. of glacial acetic acid and 5 ml. of 30% hydrogen peroxide is heated on a steam bath for 2 hours. The solvent is removed under reduced pressure to give the product of the example.

We claim:

1. A compound selected from the group consisting of those of the formula:

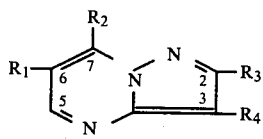

wherein $R_1$ is hydrogen or alkyl having from 1 to 3 carbon atoms; $R_2$ is selected from the group consisting of

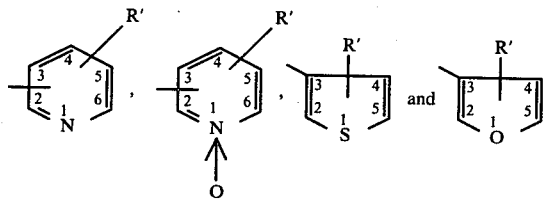

wherein R' is hydrogen or alkyl having from 1 to 3 carbon atoms; $R_3$ is hydrogen, fluoro, chloro, bromo, cyano, cyanomethyl, carbamoyl or alkyl having from 1 to 3 carbon atoms; $R_4$ is selected from the group consisting of hydrogen, fluoro, chloro, bromo, formyl, carboxyl, cyano, hydroxymethyl, N-hydroxyformimidoyl, alkyl having from 1 to 3 carbon atoms and moieties of the formulae:

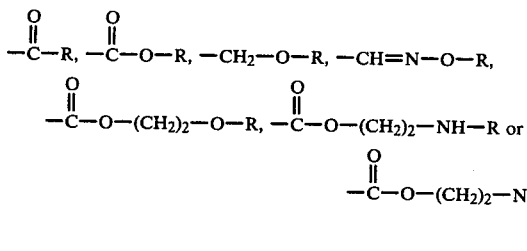

where R is alkyl having from 1 to 3 carbon atoms, and the pharmacologically acceptable acid-addition salts thereof.

2. The compound according to claim 1, 7-(3-pyridyl)-pyrazolo[1,5-a]pyrimidine.

3. The compound according to claim 1, 7-(3-pyridyl)-pyrazolo[1,5-a]pyrimidine-3-carbonitrile.

4. The compound according to claim 1, 2-ethyl-7-(3-pyridyl)pyrazolo[1,5-a]pyrimidine-3-carbonitrile.

5. The compound according to claim 1, 7-(3-pyridyl)-pyrazolo[1,5-a]pyrimidine-3-carboxylic acid ethyl ester.

6. The compound according to claim 1, 2-ethyl-7-(3-pyridyl)pyrazolo[1,5-a]pyrimidine-3-carboxylic acid ethyl ester.

7. The compound according to claim 1, 7-(3-thienyl)-pyrazolo[1,5-a]pyrimidine-3-carboxylic acid ethyl ester.

8. The compound according to claim 1, 7-(3-thienyl)-pyrazolo[1,5-a]pyrimidine-3-carbonitrile.

9. The compound according to claim 1, 6-methyl-7-(3-pyridyl)pyrazolo[1,5-a]pyrimidine-3-carbonitrile.

10. The compound according to claim 1, 3-bromo-7-(3-pyridyl)pyrazolo[1,5-a]pyrimidine.

11. The compound according to claim 1, 3-chloro-7-(3-pyridyl)pyrazolo[1,5-a]pyrimidine.

12. The compound according to claim 1, 7-(3-pyridyl)pyrazolo[1,5-a]pyrimidine, pyridine-1-oxide.

13. The compound according to claim 1, 2-methyl-7-(3-pyridyl)pyrazolo[1,5-a]pyrimidine-3-carbonitrile.

14. The compound according to claim 1, 2,6-dimethyl-7-(3-pyridyl)pyrazolo[1,5-a]pyrimidine-3-carbonitrile.

15. The compound according to claim 1, 2-methyl-7-(3-pyridyl)pyrazolo[1,5-a]pyrimidine-3-carboxylic acid ethyl ester.

16. The method of meliorating anxiety in a mammal which comprises administering internally to said mammal an effective amount of a compound of claim 1.

17. The method according to claim 16 wherein the compound is that of claim 2, 3, 4, 5, 6, 7, 8, 9, 10, 11, 12, 13, 14, or 15.

18. The compound according to claim 1, 7-(4-pyridyl)pyrazolo[1,5-a]pyrimidine-3-carbonitrile.

* * * * *